(12) United States Patent
Huang et al.

(10) Patent No.: US 12,426,972 B2
(45) Date of Patent: Sep. 30, 2025

(54) OPERATING ARM AND SURGICAL ROBOT

(71) Applicant: Shenzhen Edge Medical CO.,Ltd., Shenzhen (CN)

(72) Inventors: Jian Huang, Shenzhen (CN); Yuanqian Gao, Shenzhen (CN); Jianchen Wang, Shenzhen (CN)

(73) Assignee: Shenzhen Edge Medical CO., Ltd., Guangdong (CN)

( * ) Notice: Subject to any disclaimer, the term of this patent is extended or adjusted under 35 U.S.C. 154(b) by 571 days.

(21) Appl. No.: 17/792,189

(22) PCT Filed: Nov. 28, 2020

(86) PCT No.: PCT/CN2020/132542
§ 371 (c)(1),
(2) Date: Jul. 12, 2022

(87) PCT Pub. No.: WO2021/155704
PCT Pub. Date: Aug. 12, 2021

(65) Prior Publication Data
US 2023/0054829 A1     Feb. 23, 2023

(30) Foreign Application Priority Data

Feb. 9, 2020 (CN) .......................... 202010085505.8

(51) Int. Cl.
*A61B 34/37*     (2016.01)
*A61B 17/00*     (2006.01)

(52) U.S. Cl.
CPC .... *A61B 34/37* (2016.02); *A61B 2017/00477* (2013.01)

(58) Field of Classification Search
CPC ........ A61B 2034/302; A61B 2034/305; A61B 2034/306; A61B 34/71
See application file for complete search history.

(56) References Cited

U.S. PATENT DOCUMENTS

| | | | |
|---|---|---|---|
| 2016/0135911 A1* | 5/2016 | Yanagihara | A61B 34/37 600/102 |
| 2016/0166347 A1* | 6/2016 | Kishi | A61B 34/37 606/130 |

(Continued)

FOREIGN PATENT DOCUMENTS

| | | | | |
|---|---|---|---|---|
| CN | 104434318 A | * | 3/2015 | ....... A61B 17/00234 |
| CN | 206967474 U | * | 2/2018 | ............ B25J 9/0009 |

(Continued)

*Primary Examiner* — Benjamin J Klein
*Assistant Examiner* — Alisha J Sircar
(74) *Attorney, Agent, or Firm* — ScienBiziP, P.C.

(57) ABSTRACT

An operating arm (100) includes a driving cartridge (1), a link (2), an end instrument (3), and a first group driving wire (4) and a second group driving wire (5) penetrating the link (2). The end instrument (3) includes a connecting assembly (6) connected to the link (2) and an end effector (7) connected to the connecting assembly (6). The driving cartridge (1) includes a base (10) connected to the link (2), a first rotatable shaft (111) arranged on the base (10), and a second rotatable shaft (112) arranged on and rotating coaxially with the first rotatable shaft (111). The first group driving wire (4) starts from the first rotatable shaft (111) and terminates at a first position of the connecting assembly (6). The second group driving wire (5) starts from the second rotatable shaft (112) and terminates at a second position of the connecting assembly (6).

19 Claims, 10 Drawing Sheets

(56) References Cited

U.S. PATENT DOCUMENTS

| | | | |
|---|---|---|---|
| 2017/0051729 A1* | 2/2017 | Manfredi | A61B 34/30 |
| 2019/0208989 A1* | 7/2019 | Xu | A61B 17/00234 |
| 2020/0093554 A1* | 3/2020 | Schuh | A61B 17/00234 |
| 2020/0107898 A1* | 4/2020 | Kim | A61B 1/018 |

FOREIGN PATENT DOCUMENTS

| | | | | |
|---|---|---|---|---|
| CN | 110269686 A | * | 9/2019 | A61B 34/37 |
| CN | 110269694 A | * | 9/2019 | A61B 34/37 |
| CN | 211911796 U | | 11/2020 | |

* cited by examiner

OPERATING ARM AND SURGICAL ROBOT

FIELD

The present disclosure claims priority of a Chinese patent application No. CN 202010085505.8, and titled "operating arm and surgical robot" filed on Feb. 9, 2020 in China. All disclosures of the Chinese patent application may be quoted by the present disclosure.

The subject matter herein generally relates to surgical systems, in particular to an operating arm and a surgical robot.

BACKGROUND

Minimally invasive surgery refers to a surgical method of performing a procedure in a human body cavity using modem medical instruments such as laparoscopes, thoracoscopes, and so on. Compared with traditional surgery modes, minimally invasive surgery has advantages of being small in trauma, light in pain, fast in recovery, and the like.

With advances in science and technology, minimally invasive surgical technologies are increasingly mature and widely used. A typical minimally invasive surgical robot includes a master console and a slave operating device, the master console is used for sending a control command to the slave operating device according to the doctor's operation to control the slave operating device, and the slave operating device is used for responding to the control command of the master console, and making corresponding surgical operations.

The slave operating device usually includes a robot arm, a power mechanism, and an operating arm provided on the robot arm. The robot arm is configured for adjusting a position of the operating arm, the operating arm is configured for reaching the patient body and making the surgical operations, and the power mechanism is configured for driving an end instrument of the operating arm to perform the corresponding surgical operations. However, during performing surgical operation, due to structural limitation of end instruments, current operating arms do not have enough flexibility. Therefore, increasing the flexibility of the operating arm during the surgical operation is the problem to be solved.

SUMMARY

A main purpose of the present application is to provide an operating arm and a surgical robot, aimed at improving the flexibility of the operating arm during minimally invasive surgical operations.

To achieve the above object, the present application provides an operating arm, which includes successively connected a driving cartridge, a link, an end instrument, and a first group and a second group of driving wire penetrating the link. The end instrument includes a connecting assembly connected to the link and an end effector connected to the link. The driving cartridge includes a base connected to the link, and a driving shaft assembly arranged on the base. The driving shaft assembly includes a first rotatable shaft arranged on the base, and a second rotatable shaft arranged on the first rotatable shaft and coaxially rotated with the first rotatable shaft, a first driving wire starting from the first rotatable shaft and terminating at a first positon of the connecting assembly, a second driving wire starting from the second rotatable shaft and terminating at a second position of the connecting assembly, the first position is farther away the link, the second position is nearer to the link, thereby the first group of driving wire and the second group of driving wire driving the end instrument to move in a direction corresponding to a degree of freedom during the rotation of the driving shaft assembly.

To achieve the above object, the present application further provides a surgical robot, the surgical robot includes the above operating arm.

The operating arms and the surgical robots provided herein, the first group of driving wire starting from the first rotatable shaft and terminating at a first position of the connecting assembly, the second group of driving wire starting from the second rotatable shaft and terminating at a second position of the connecting assembly, thus different driving wires have different starting positions and different terminating positions to allow the connecting assembly to move in different directions and different degrees, thereby the first group of driving wire and the second group of driving wire drive the end instrument to move in a direction corresponding to a degree of freedom, and thus the flexibility of the operating arm during operation is improved.

REFERENCE NUMERAL DESCRIPTION

| Reference numeral | Name | Reference numeral | Name | Reference numeral | Name |
|---|---|---|---|---|---|
| 100 | operating arm | 1 | driving cartridge | 2 | link |
| 3 | end instrument | 4 | first group of driving wire | 5 | second group of driving wire |
| 6 | connecting assembly | 7 | end effector | 61 | first connecting unit |
| 62 | second connecting unit | 63 | third connecting unit | 64 | fourth connecting unit |
| 65 | fifth connecting unit | 10 | base | 11 | driving shaft assembly |
| 113 | pitch driving shaft assembly | 114 | yaw driving shaft assembly | 115 | first thick shaft |
| 116 | first thin shaft | 41 | first driving wire | 42 | second driving wire |
| 43 | third driving wire | 44 | fourth driving wire | 51 | fifth driving wire |
| 52 | sixth driving wire | 53 | seventh driving wire | 54 | eighth driving wire |
| 611 | first through hole | 612 | second through hole | 615 | fifth through hole |
| 616 | sixth through hole | 633 | third through hole | 634 | fourth through hole |
| 637 | seventh through hole | 638 | eighth through hole | 661 | first resident hole |
| 662 | second resident hole | 663 | third resident hole | 664 | fourth resident hole |
| 81 | first continuous driving wire | 82 | second continuous driving wire | 83 | first connecting wire |
| 84 | second connecting wire | 111 | first rotatable shaft | 112 | second rotatable shaft |
| 60 | connecting unit | 200 | rotatable portion | 300 | first connecting portion |
| 400 | second connecting portion | 210 | rotatable shaft | 220 | connecting element |

DETAILED DESCRIPTION

For ease of understanding of the present application, the present application will be described more fully hereinafter with reference to the associated drawings. Preferred embodiments of the present application are set forth in the accompanying drawings. This application may, however, be embodied in many different forms and is not limited to the embodiments described herein. Rather, these embodiments are provided for the purpose of providing a more thorough and thorough understanding of the disclosure of the present application.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purposes of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure.

Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items.

The present application provides a surgical robot, the surgical robot includes a master console and a slave operating device. The master console is used for sending control commands to the slave operating device according to the operation of a surgeon to control the slave operating device. The slave operating device is used for responding to the control commands sent by the master console and performing corresponding operations. The slave operating device includes a robot arm, a power mechanism, and an operating arm provided on the robot arm. The operating arm is configured for reaching the patient body to perform the corresponding surgical operations under the driving of the power mechanism.

Figure 1:
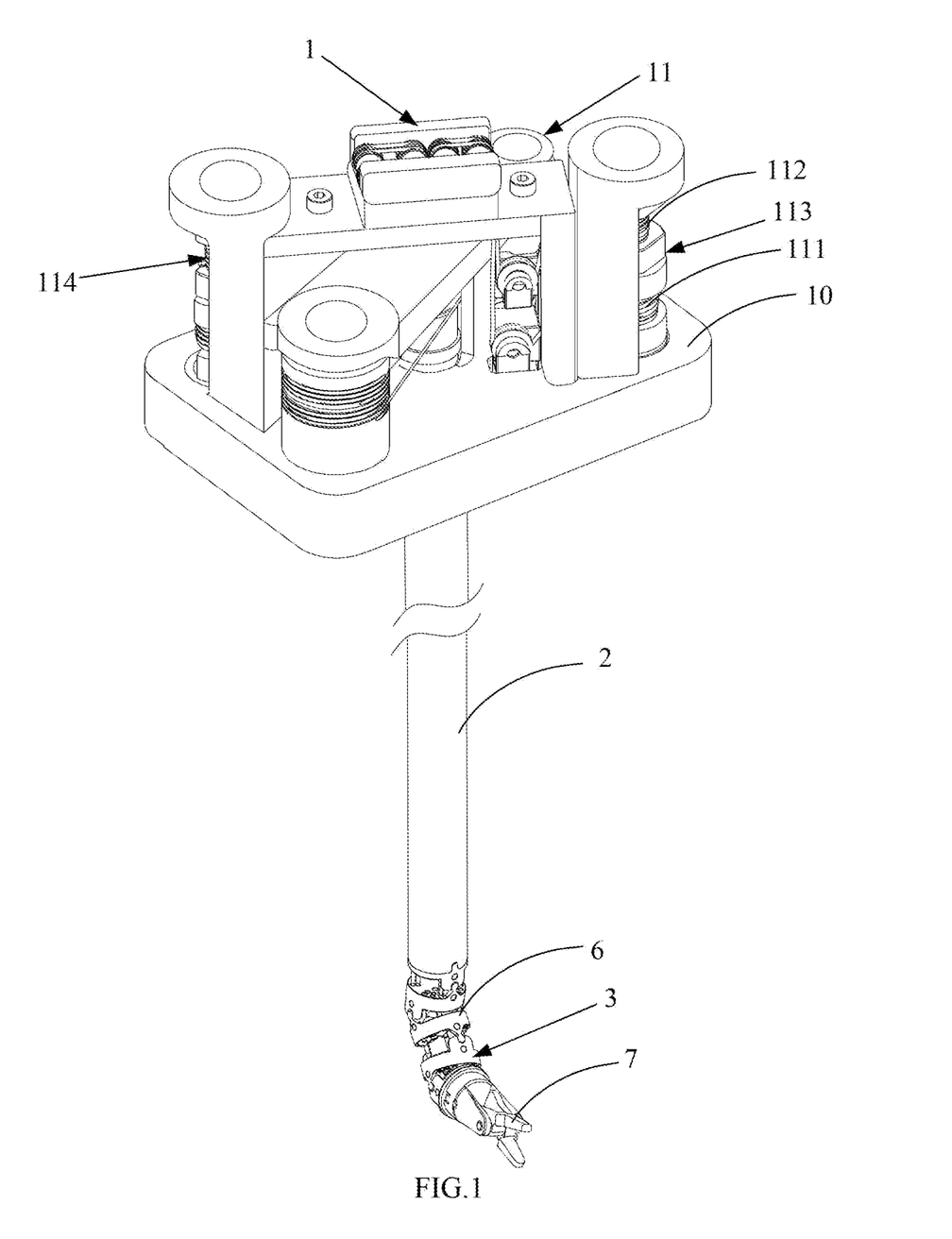
FIG. 1 is a schematic structural view of an operating arm according to an embodiment of the present application.
Figure 2:
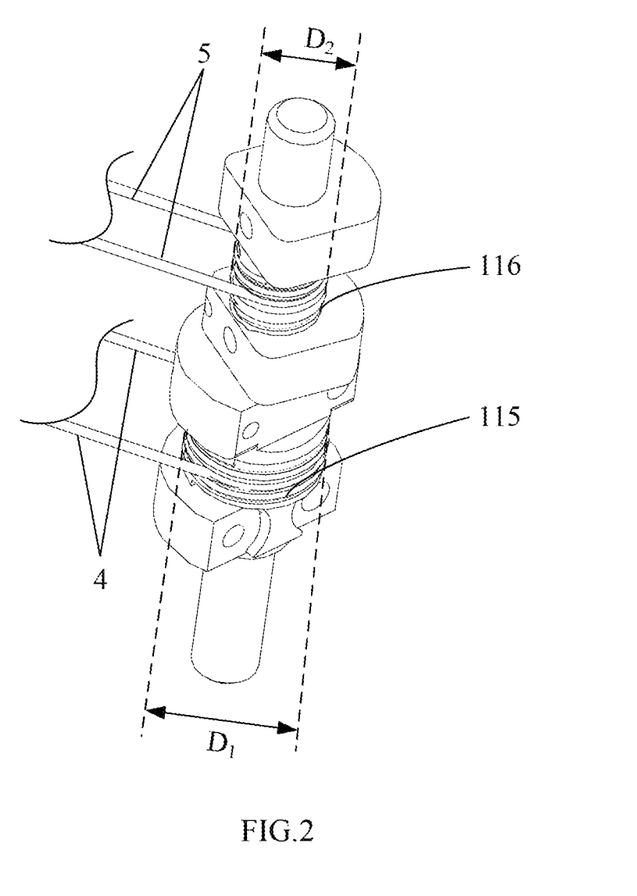
FIG. 2 is a schematic partial view of a pitch driving shaft assembly or a yaw driving shaft assembly of the operating arm in FIG. 1 according to an embodiment.

Referring to FIG. 1 and FIG. 2, an operating arm 100 includes successively connected a driving cartridge 1, a link 2, an end instrument 3, and a first group of driving wire 4 and a second group of driving wire 5 penetrating the link 2. The end instrument 3 includes a connecting assembly 6 connected to the link 2 and an end effector 7 connected to the connecting assembly 6.

Figure 3:
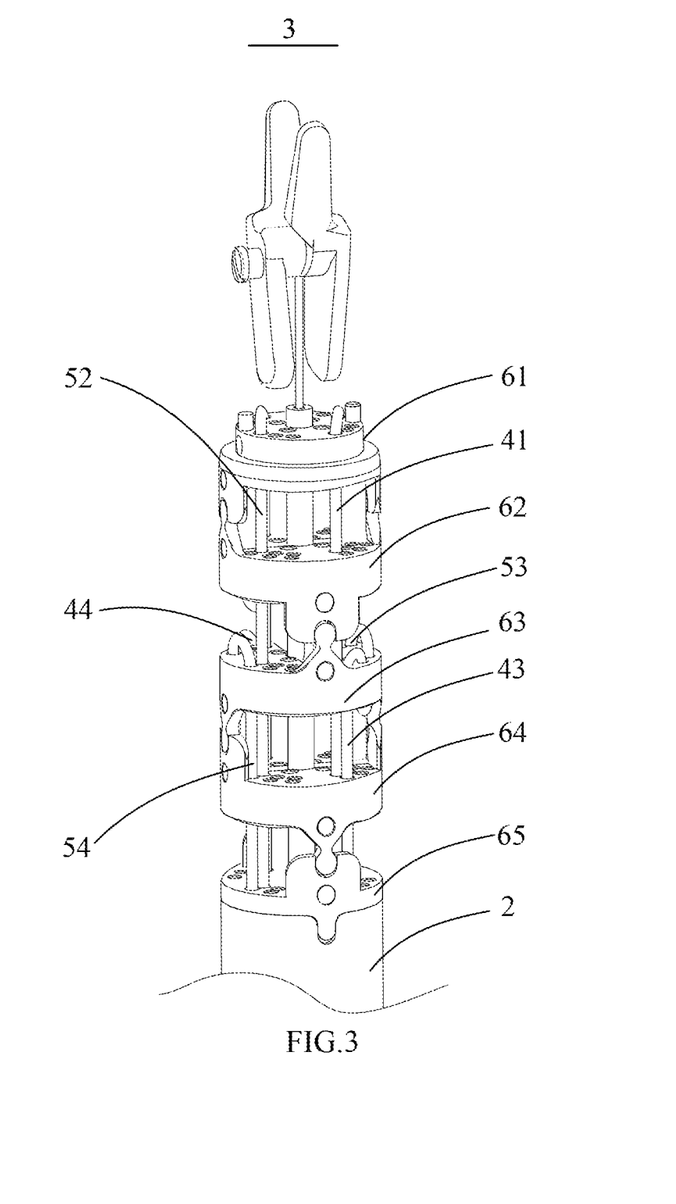
FIG. 3 is a schematic view of an end instrument of the operating arm in FIG. 1 according to a first embodiment.

Referring to FIG. 3, the connecting assembly 6 includes a first connecting unit 61 connected to the end effector 7, a second connecting unit 62 coupled to the first connecting unit 61, a third connecting unit 63 coupled to the second connecting unit 62, a fourth connecting unit 64 coupled to the third connecting unit 63, and a fifth connecting unit 65 having one end connected to the fourth connecting unit 64 and another end connected to the link 2. Of course, in other embodiments, the connecting units of the connecting assembly 6 are not limited to five as listed above, and other numbers of the connecting units that can implement the same scheme of the present application are also included within the scope of the present application.

Figure 4:
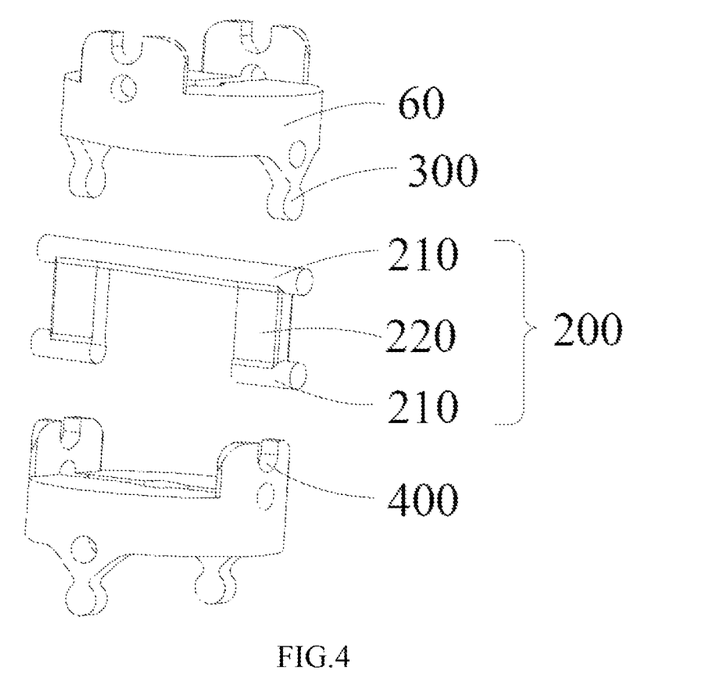
FIG. 4 is a schematic partial view of a connecting assembly of the operating arm in FIG. 1.

Referring again to FIG. 3, the first group of driving wire 4 terminates at the first connecting unit 61, and the second group of driving wire 5 terminates at the third connecting unit 63. Referring to FIG. 4, the connecting assembly 6 includes a connecting unit 60 and a rotatable portion 200. In particular, the connecting unit 60 may have a connecting portion (not shown), configured for matching to a connecting portion of an adjacent connecting unit 60. In one embodiment, the connecting portion includes a first connecting portion 300 and/or a second connecting portion 400, configured for respectively matching to a second connecting portion 400 and/or a first connecting portion 300 of the adjacent connecting unit 60. The rotatable portion 200 includes two rotatable shafts 210 and a connecting element 220 connecting the two rotatable shafts 210. The rotatable shafts 210 are configured for connecting two adjacent connecting units 60, to allow the two adjacent connecting units 60 rotatable relative to each other, and thus form a joint assembly. In particular, the connecting element 220 makes a distance between the two rotatable shafts 210 unchanged, when the joint assembly rotates, the distance between the two rotatable shafts 210 is maintained unchanged, and the first connecting portion 300 and the second connecting portion 400 can have a movement relative to each other. In one embodiment, the first connecting portion 300 can rotate relative to the second connecting portion 400, and the first connecting portion 300 can move along the second connecting portion 400.

Figure 5:
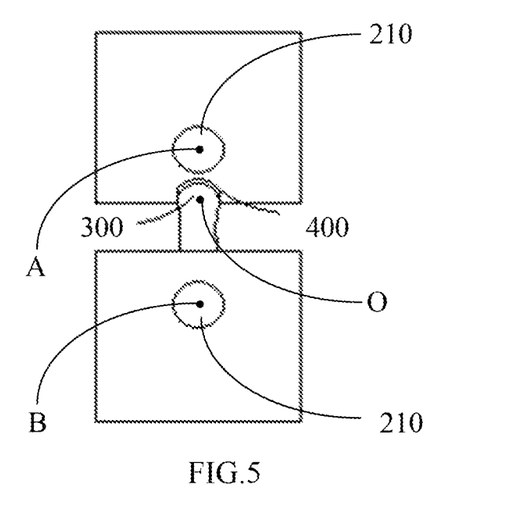
FIG. 5 is a simplified structural view from a side viewing the connecting assembly of FIG. 4.

Referring to FIG. 5, a joint assembly has three rotatable shafts, centers of the three rotatable shafts are at A line, O line, and B line, and the A line, the O line, and the B line cooperatively form central axes of the connecting units during rotation. In one embodiment, for convenience for illustration and calculation, the A line, the O line, and the B line is considered to be A point, O point, and B point, and the rotation central axes can be defined by the A point connected to the B point (AB connection), then a line through the O point is formed perpendicular to the AB connection, the intersection between the AB connection and the line through the O point can be considered to be the rotation central axis. In particular, a rotation central axis between the first connecting unit and the second connecting unit may be parallel with a rotation central axis between the third connecting unit and the fourth connecting unit, and a rotation central axis between the second connecting unit and the third connecting unit is parallel with a rotation central axis between the fourth connecting unit and the fifth connecting unit, with the rotation central axis between the first connecting unit and the second connecting unit perpendicular to the rotation central axis between the second connecting unit and the third connecting unit. It can be understood that the above rotation central axes are rotation centers of the respective connecting units during rotation, and during rotation, the rotation central axes of the connecting units may be changed along a movement track during the rotation. In particular, the first connecting unit 61 has a same rotation direction relative to the second connecting unit 62 with that of the third connecting unit 63 relative to the fourth connecting unit 64, the second connecting unit 62 has a same rotation direction relative to the third connecting unit 62 with that of the fourth connecting unit 64 relative to the fifth connecting unit 65, and the first connecting unit 61 and the third connecting unit 63 are in an orthogonal state in the rotation direction relative to the neighboring connecting units of the second connecting unit 62 and the fourth connecting unit 64 relative to the neighboring connecting units.

It can be understood that the present application does not limit the above orthogonal state, in other embodiments, it is also possible to other non-orthogonal states. In addition, the first connecting unit 61, the second connecting unit 62, the third connecting unit 63, the fourth connecting unit 64, and the fifth connecting unit 65 are provided with a plurality of through holes in the corresponding positions, for the first group of driving wire 4 and the second group of driving wire 5 passing therethrough.

Referring again to FIGS. 1 and 2, the driving cartridge 1 includes a base 10, the link 2 extending from the base 10, and a driving shaft assembly 11 arranged on the base 10.

Specially, as shown in FIG. 1, the driving shaft assembly 11 includes a first rotatable shaft 111, and a second rotatable shaft 112 arranged on the first rotatable shaft 111 and rotating coaxially with the first rotatable shaft 111. The second rotatable shaft 112 can be adjusted relative to the first rotatable shaft 111, to adjust the gesture of the end instrument 3 to an initial state. It will be appreciated that when it is necessary to adjust the gesture to the initial state of the end instrument 3, the respective connecting units of the end instrument 3 can be clamped using a zero-bit tooling adjustment member (not shown) to enable each connecting unit maintain a straight state; at this time, if the posture of the end instrument 3 is still not in the initial state, the position between the first rotatable shaft 111 and the second rotatable shaft 112 can be further adjusted, to allow the end instrument 3 back to the initial state.

The first group of driving wire 4 starts from the first rotatable shaft 111 and terminates at a first position of the connecting assembly 6, the second group of driving wire 5 starts from the second rotatable shaft 112 and terminates at a second position of the connecting assembly 6. The first position is farther away from the link 2, and the second position is nearer to the link 2.

In the present embodiment, a diameter of the first rotatable shaft 111 is greater than that of the second rotatable shaft 112. In this way, when the first rotatable shaft 111 and the second rotatable shaft 112 are rotated the same number, a length of the first group of driving wire 4 released/tensioned by the first rotatable shaft 111 is greater than a length of the second group of driving wire 5 released/tensioned by the second rotatable shaft 112. Thus, the rotation amplitude of the first connecting unit 61 is greater than the rotation amplitude of the third connecting unit 63, thereby causing the end instrument 3 to be more flexible in pitch or yaw movement degrees of freedom. Of course, in other embodiments, the diameter of the first rotatable shaft 111 may also be equal to the diameter of the second rotatable shaft 112.

It will be appreciated that the driving shaft assembly 11 can be a pitch driving shaft assembly or a yaw driving shaft assembly. If the driving shaft assembly 11 is a pitch driving shaft assembly, when it is rotated, the first group of driving wire 4 and the second group of driving wire 5 drive the end instrument 3 to pitch. If the driving shaft assembly 11 is a yaw driving shaft assembly, when it is rotated, the first group of driving wire 4 and the second group of driving wire 5 drive the end instrument 3 to yaw. Of course, the first group of driving wire 4 corresponding to the pitch driving shaft assembly and the yaw driving shaft assembly can have different terminal positions at the first connecting unit 61, the second group of driving wire 5 corresponding to the pitch driving shaft assembly and the yaw driving shaft assembly can have different terminal positions at the third connecting unit 63.

The driving shaft assembly 11 may include both the pitch driving shaft assembly and the yaw driving shaft assembly, this will be described in detail below.

Referring again to FIG. 1, the driving shaft assembly 11 includes both a pitch driving shaft assembly 113 and a yaw driving shaft assembly 114 arranged oppositely on the base 10, the pitch driving shaft assembly 113 and the yaw driving shaft assembly 114 may have the same structure, therefore, in the drawings, the pitch driving shaft assembly 113 is mainly labeled. Referring to FIG. 2, the pitch driving shaft assembly 113 includes a first thick shaft 115 disposed on the base 10, and a first thin shaft 116 arranged on the first thick shaft 115 and rotating coaxially with the first thick shaft 115.

Figure 8:
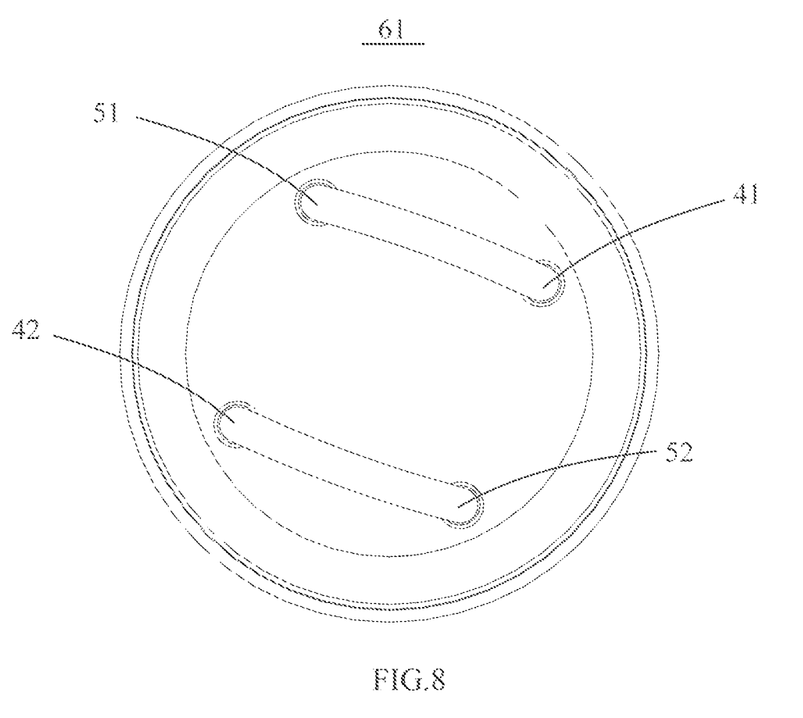
FIG. 8 is a schematic view of a first connecting unit of the end instrument in FIG. 3 from a top view according to an embodiment.
Figure 9:
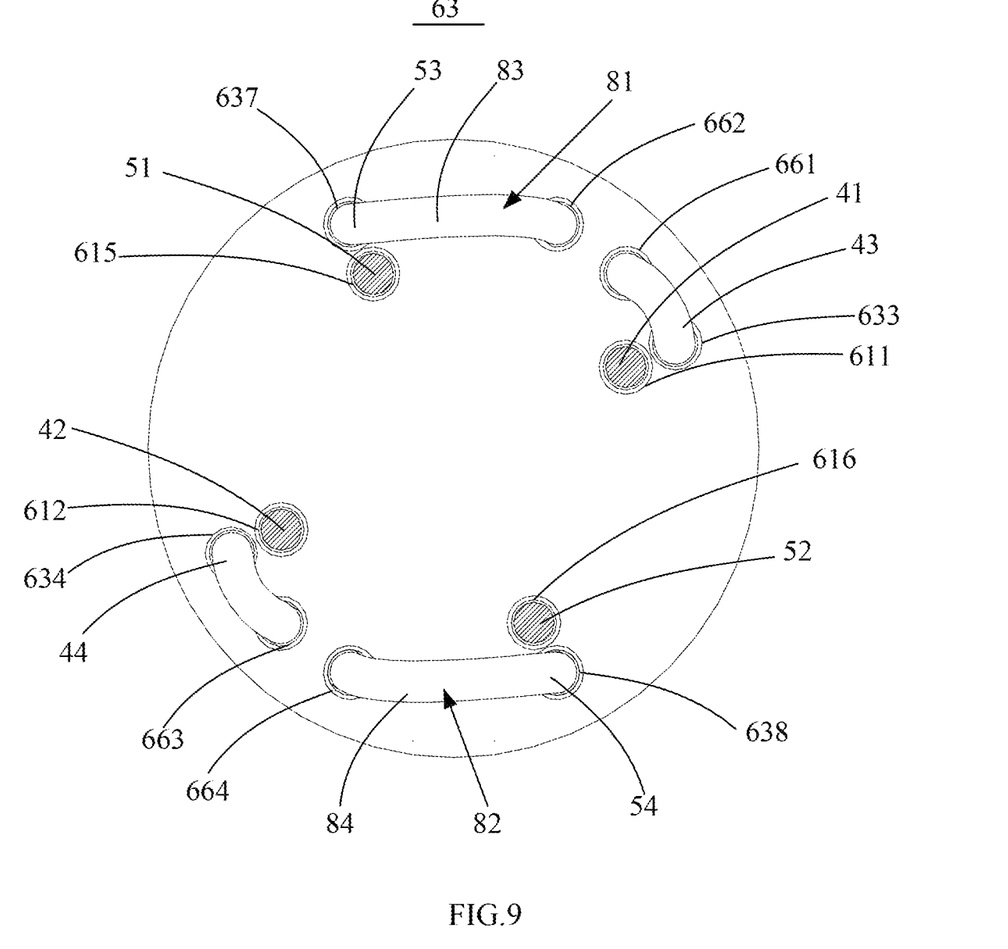
FIG. 9 is a schematic view of a third connecting unit of the end instrument in FIG. 3 from a top view according to an embodiment.

Referring to FIGS. 8 and 9, the first group of driving wire 4 includes a first driving wire 41 and a second driving wire 42 both starting from the first thick shaft 115 but in an inverse winding direction, and a third driving wire 43 and a fourth driving wire 44 both starting from the first thin shaft 116 and having an inverse winding direction. The yaw driving shaft assembly 114 includes a second thick shaft (not labeled) disposed on the base 10, and a second thin shaft (not labeled) arranged on the second thick shaft and rotating coaxially with the second thick shaft. The second group of driving wire 5 includes a fifth driving wire 51 and a sixth driving wire 52 both starting from the second thick shaft but in an inverse winding direction, and a seventh driving wire 53 and an eighth driving wire 54 both starting from the second thin shaft but in an inverse winding direction.

In particular, the first driving wire 41, the second driving wire 42, the fifth driving wire 51, and the sixth driving wire 52 each terminate at the first connecting unit 61; and the third driving wire 43, the fourth driving wire 44, the seventh driving wire 53, and the eighth driving wire 54 each terminate at the third connecting unit 63. It can be understood that the present application is not limited to eight driving wires, and other numbers of the driving wires that can be implemented in the present application are also included in the scope of the present application.

Figure 6:
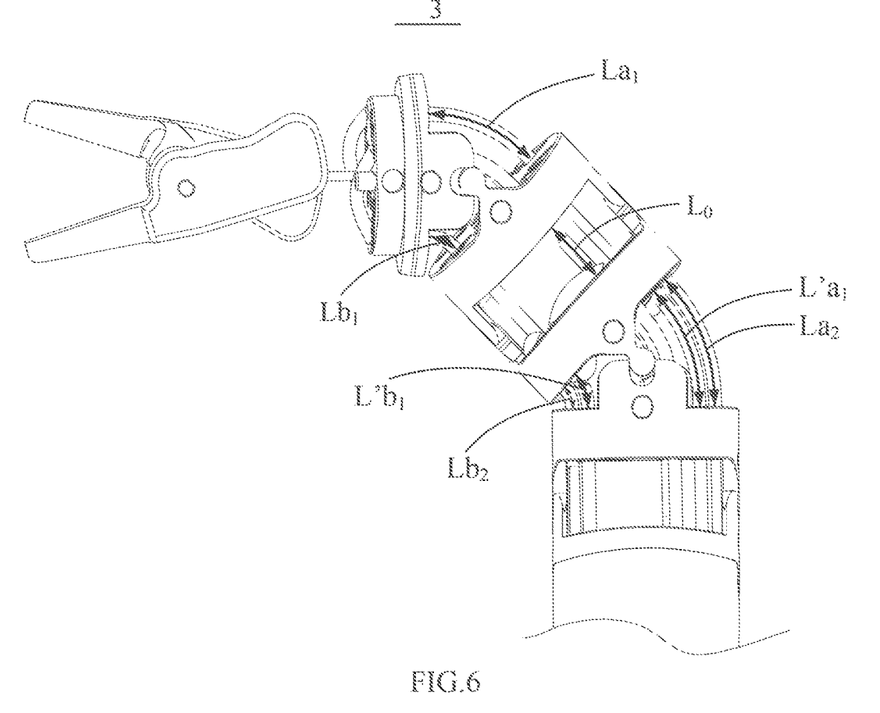
FIG. 6 is a schematic view of the end instrument of FIG. 3 implementing a pitch movement degree of freedom according to an embodiment.

Referring to FIG. 6, the pitch driving shaft assembly 113 drives the end instrument 3 to implement the pitch degrees of freedom, a length variation $\Delta L_{41}$ of the first driving wire 41 is equal to a sum of a first length variation $\Delta La_1$ and a second length variation $\Delta L'a_1$, that is, $\Delta L_{41}=\Delta La_1+\Delta L'a_1$. In particular, the first length variation $\Delta La_1$ refers to a length variation ($\Delta La_1=La_1-L_0$) of a portion of the first driving wire 41 between the first connecting unit 61 and the second connecting unit 62, the second length variation $\Delta L'a_1$ refers to a length variation ($\Delta L'a_1=L'a_1-L_0$) of a portion of the first driving wire 41 between the third connecting unit 63 and the fourth connecting unit 64.

A length variation $\Delta L_{42}$ of the second driving wire 42 is equal to a sum of a third length variation $\Delta Lb_1$ and a fourth length variation $\Delta L'b_1$, that is. $\Delta L_{42}=\Delta Lb_1+\Delta L'b_1$. In particular, the third length variation $\Delta Lb_1$ refers to a length variation ($\Delta Lb_1=L_0-Lb_1$) of a portion of the second driving wire 42 between the first connecting unit 61 and the second connecting unit 62, the fourth length variation $\Delta L'b_1$ refers to a length variation ($\Delta L'b_1=L_0-L'b_1$) of a portion of the second driving wire 42 between the third connecting unit 63 and the fourth connecting unit 64.

A fifth length variation $\Delta La_2$ of the third driving wire 43 is equal to a sixth length variation $\Delta Lb_2$ of the fourth driving wire 44, the fifth length variation $\Delta La_2$ refers to a length variation ($\Delta La_2=La_2-L_0$) of a portion of the third driving wire 43 between the third connecting unit 63 and the fourth connecting unit 64, that is, the sixth length variation $\Delta Lb_2$ refers to a length variation ($\Delta Lb_2=L_0-Lb_2$) of a portion of the fourth driving wire 44 between the third connecting unit 63 and the fourth connecting unit 64.

In particular, the first length variation $\Delta La_1$ is equal to the third length variation $\Delta Lb_1$, that is, $\Delta La_1=\Delta Lb_1$. The second length variation $\Delta L'a_1$ is equal to the fourth length variation $\Delta L'b_1$, that is, $\Delta L'a_1=\Delta L'b_1$; a sum of the first length variation $\Delta La_1$ and the second length variation $\Delta L'a_1$ is equal to a sum of the third length variation $\Delta Lb_1$ and the fourth length variation $\Delta L'b_1$, that is: $\Delta La_1+\Delta L'a_1=\Delta Lb_1+\Delta L'b_1$.

In addition, it will be appreciated that $La_1+Lb_1=2L_0$, $L'a_1+L'b_1=2L_0$, $La_2+Lb_2=2L_0$.

It should be understood that the above $L_0$ refers to an initial length of the driving wire between adjacent connecting assemblies, in this embodiment, the distance between different adjacent connecting assemblies can be the same, i.e., the initial length of the driving wire between the respective adjacent connecting assemblies can be the same. In other embodiments, the distance between different adjacent connecting assemblies may be different.

It will be appreciated that when the end instrument 3 implements the movement of the pitch degrees of freedom, a length of the first driving wire 41 and the second driving wire 42 between the second connecting unit 62 and the third connecting unit 63, and a length of the first driving wire 41 and the second driving wire 42 between the fourth connecting unit 64 and the fifth connecting unit 65 are unchanged, and a length of the third driving wire 43 and the fourth driving wire 44 between the fourth connecting unit 64 and the fifth connecting unit 65 are unchanged.

As shown in FIG. 2, a diameter ratio $D_1/D_2$ of the first thick shaft 115 and the first thin shaft 116, is equal to a ratio of the length variation $\Delta L_{41}$ of the first driving wire 41 and the fifth length variation $\Delta La_2$ of the third driving wire 43, that is, $D_1/D_2=\Delta L_{41}/\Delta La_2$, or equal to a ratio of the length variation $\Delta L_{42}$ of the second driving wire 42 and the sixth length variation $\Delta Lb_2$ of the fourth driving wire 44, that is, $D_1/D_2=\Delta L_{42}/\Delta Lb_2$.

Figure 7:
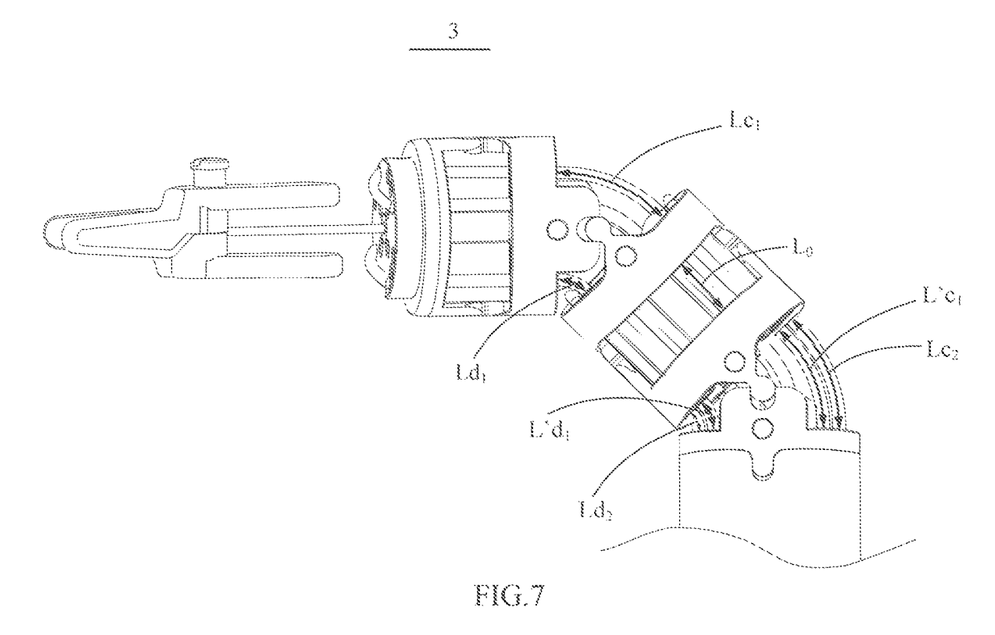
FIG. 7 is a schematic view of the end instrument of FIG. 3 implementing a yaw movement degree of freedom according to an embodiment.

Referring to FIG. 7, the yaw driving shaft assembly 114 drives the end instrument 3 to implement the yaw degrees of freedom, a length variation $\Delta L_{51}$ of the fifth driving wire 51 is equal to a sum of a seventh length variation $\Delta Lc_1$ and an eighth length variation $\Delta L'c_1$, that is, $\Delta L_{51}=\Delta Lc_1+\Delta L'c_1$. The seventh length variation $\Delta Lc_1$ is a length variation of a portion of the fifth driving wire 51 between the second connecting unit 62 and the third connecting unit 63, and the eighth length variation $\Delta L'c_1$ is a length variation of a portion of the fifth driving wire 51 between the fourth connecting unit 64 and the fifth connecting unit 65.

A length variation $\Delta L_{52}$ of the sixth driving wire 52 is equal to a sum of a ninth length variation $\Delta Ld_1$ and a tenth length variation $\Delta L'd_1$, that is, $\Delta L_{52}=\Delta Ld_1+\Delta L'd_1$. The ninth length variation $\Delta Ld_1$ is a length variation of a portion of the sixth driving wire 52 between the second connecting unit 62 and the third connecting unit 63, and the tenth length variation $\Delta L'd_1$ is a length variation of a portion of the sixth driving wire 52 between the fourth connecting unit 64 and the fifth connecting unit 65.

An eleventh length variation $\Delta Lc_2$ of the seventh driving wire 53 is equal to a twelfth length variation $\Delta Ld_2$ of the eighth driving wire 54, the eleventh length variation $\Delta Lc_2$ is a length variation ($\Delta Lc_2=Lc_2-L_0$) of a portion of the seventh driving wire 53 between the fourth connecting unit 64 and the fifth connecting unit 65, and the twelfth length variation $\Delta Ld_2$ is a length variation ($\Delta Ld_2=Ld_2-L_0$) of a portion of the eighth driving wire 54 between the fourth connecting unit 64 and the fifth connecting unit 65.

In particular, the seventh length variation $\Delta Lc_1$ is equal to the ninth length variation $\Delta Ld_1$, that is $\Delta Lc_1=\Delta Ld_1$. The eighth length variation $\Delta L'c_1$ is equal to the tenth length variation $\Delta L'd_1$, that is, $\Delta L'c_1=\Delta L'd_1$. A sum of the seventh length variation $\Delta Lc_1$ and the eighth length variation $\Delta L'c_1$, is equal to a sum of the ninth length variation $\Delta Ld_1$ and the tenth length variation $\Delta L'd_1$, that is: $\Delta Lc_1+\Delta L'c_1=\Delta Ld_1+\Delta L'd_1$.

In addition, it will be appreciated that $Lc_1+Ld_1=2L_0$, $L'c_1+L'd_1=2L_0$, $Lc_2+Ld_2=2L_0$.

It should be understood that the above $L_0$ refers to an initial length of the driving wire between adjacent connecting components, in this embodiment, the distance between the different adjacent connecting assemblies can be the same, that is, the initial length of the driving wire between the respective adjacent connecting assemblies can be the same. In other embodiments, the distance between different adjacent connecting components can also be different.

It will be appreciated that when the end instrument 3 implements the movement of yaw degrees of freedom, a length of the fifth driving wire 51 and the sixth driving wire 52 between the first connecting unit 61 and the second connecting unit 62, and a length of the fifth driving wire 51 and the sixth driving wire 52 between the third connecting unit 63 and the fourth connecting unit 64 are unchanged.

A ratio of the second thick shaft and the second thin shaft $D_3/D_4$ (not shown), is equal to a ratio of the length variation $\Delta L_{51}$ of the fifth driving wire 51 and the eleventh length variation $\Delta Lc_2$ of the seventh driving wire 53, that is, $D_3/D_4 = \Delta L_{51}/\Delta Lc_2$; or equal to a ratio of the length variation $\Delta L_{52}$ of the sixth driving wire 52 and the twelfth length variation $\Delta Ld_2$ of the eighth driving wire 54, that is, $D_3/D_4 = \Delta L_{52}/\Delta Ld_2$.

The connecting assembly 6 has an axis and is coaxially with an axis of the link 2, therefore, the axis of the link 2 is described as a reference in the following. Referring to FIGS. 8 and 9, the first connecting unit 61 is provided with a first through hole 611 and a second through hole 612 at an outer periphery thereof and arranged opposite to the axis of the link 2, the first through hole 611 is used for the first driving wire 41 passing therethrough, and the second through hole 612 is used for the second driving wire 42 passing therethrough. That is, the first driving wire 41 and the second driving wire 42 are arranged on the first connecting unit 61 and surrounding the axis of the link 2. Similarly, the first connecting unit 61 is provided with a fifth through hole 615 and a sixth through hole 616 at an outer periphery thereof and arranged opposite to the axis of the link 2, the fifth through hole 615 is used for the fifth driving wire 51 passing therethrough, and the sixth through hole 616 is used for the sixth driving wire 52 passing therethrough. That is, the fifth driving wire 51 and the sixth driving wire 52 are arranged on the first connecting unit 61 and surrounding the axis of the link 2. In particular, the fifth through hole 615 and the sixth through hole 616 are disposed each adjacent to the first through hole 611 and the second through hole 612.

Specifically, as shown in FIG. 9, the third connecting unit 63 is provided with a third through hole 633 and a fourth through hole 634 at an outer periphery thereof and arranged opposite to the axis of the link 2. The third through hole 633 is used for the third driving wire 43 passing therethrough, and the fourth through hole 634 is used for the fourth driving wire 44 passing therethrough. That is, the third driving wire 43 and the fourth driving wire 44 are arranged on the third connecting unit 63 and surrounding the axis of the link 2. Similarly, the third connecting unit 63 is provided with a seventh through hole 637 and an eighth through hole 638 at an outer periphery thereof and arranged opposite to the axis of the link 2. The seventh through hole 637 is used for the seventh driving wire 53 passing therethrough, and the eighth through hole 638 is used for the eighth driving wire 54 passing therethrough. That is, the seventh driving wire 53 and the eighth driving wire 54 are arranged on the third connecting unit 63 and surrounding the axis of the link 2.

The third connecting unit 63 is also provided with a first through hole 611, a second through hole 612, a fifth through hole 615, and a sixth through hole 616 corresponding to those of the first connecting unit 61, and the first through hole 611, the second through hole 612, the fifth through hole 615, and the sixth through hole 616 are located at an inner side of the third through hole 633, the fourth through hole 634, the seventh through hole 637, and the eighth through hole 638 at the third connecting unit 63. The first through hole 611 is disposed adjacent to the third through hole 633, the second through hole 612 is disposed adjacent to the fourth through hole 634, the fifth through hole 615 is disposed adjacent to the seventh through hole 637, and the sixth through hole 616 is disposed adjacent to the eighth through hole 638. That is, the first driving wire 41 is adjacent to the third driving wire 43, the second driving wire 42 is adjacent to the fourth driving wire 44, the fifth driving wire 51 is adjacent to the seventh driving wire 53, the sixth driving wire 52 is adjacent to the eighth driving wire 54, respectively, and the third driving wire 43, the fourth driving wire 44, the seventh driving wire 53, and the eighth driving wire 54 are relatively located adjacent to a periphery of the third connecting unit 63.

Referring to FIG. 9, the third connecting unit 63 has a first resident hole 661 and a second resident hole 662 located between the third through hole 633 and the seventh through hole 637, that is, the first resident hole 661 and the second resident hole 662 are located between the third driving wire 43 and the seventh driving wire 53. The first resident hole 661 and the second resident hole 662 may both be adjacent to the third through hole 633. Of course, in other embodiments, the first resident hole 661 and the second resident hole 662 may be adjacent to the seventh through hole 637, the first resident hole 661 may be adjacent to the third through hole 633, and the second resident hole 662 may be adjacent to the seventh through hole 637.

The third connecting unit 63 is also provided with a third resident hole 663 and a fourth resident hole 664 located between the fourth through hole 634 and the eighth through hole 638, that is, the third resident hole 663 and the fourth resident hole 664 are located between the fourth driving wire 44 and the eighth driving wire 54. The third resident hole 663 and the fourth resident hole 664 may both be adjacent to the fourth through hole 634. Of course, in other embodiments, the third resident hole 663 and the fourth resident hole 664 may be provided adjacent to the eighth through hole 638, the third resident hole 663 may be adjacent to the fourth through hole 634, and the fourth resident hole 664 may be adjacent to the eighth through hole 638.

In one embodiment, as shown in FIG. 8, the first driving wire 41 and the fifth driving wire 51 cooperatively form a continuous driving wire, the second driving wire 42 and the sixth driving wire 52 cooperatively form a continuous driving wire. As shown in FIG. 9, the third driving wire 43 and the seventh driving wire 53 are in a complete first continuous driving wire 81, the fourth driving wire 44 and the eighth driving wire 54 are in a complete second continuous driving wire 82. It will be appreciated that the third driving wire 43 and the seventh driving wire 53 actually belong to the same driving wire with only different sections of the same driving wire. In the same way, the fourth driving wire 44 and the eighth driving wire 54 actually belong to the same driving wire, but only different sections of the same driving wire. Thus, the driving function of the driving shaft assembly 11 can be realized by less driving wires, and therefore, the manufacturing process of the driving wire is reduced.

In particular, the first continuous driving wire 81 includes a first connecting wire 83 that is coupled to the third driving wire 43 and the seventh driving wire 53, one end of the first connecting wire 83 is connected to the third driving wire 43, and the other end is sequentially passed through the first resident hole 661 and the second resident hole 662 to be connected to the seventh driving wire 53. That is, the first continuous driving wire 81 sequentially passes through the third through hole 633, the first resident hole 661, the second resident hole 662, and the seventh through hole 637 to form a "W" form.

The second continuous driving wire 82 includes a second connecting wire 84 that is coupled to the fourth driving wire 44 and the eighth driving wire 54, and one end of the second connecting wire 84 is connected to the fourth driving wire 44, the other end passes through the third resident hole 663 and the fourth resident hole 664 to be connected to the eighth driving wire 54. That is, the second continuous driving wire 82 sequentially passes through the fourth through hole 634, the third resident hole 663, the fourth resident hole 664, and the eighth through hole 638 to form a "W" form.

Figure 10:
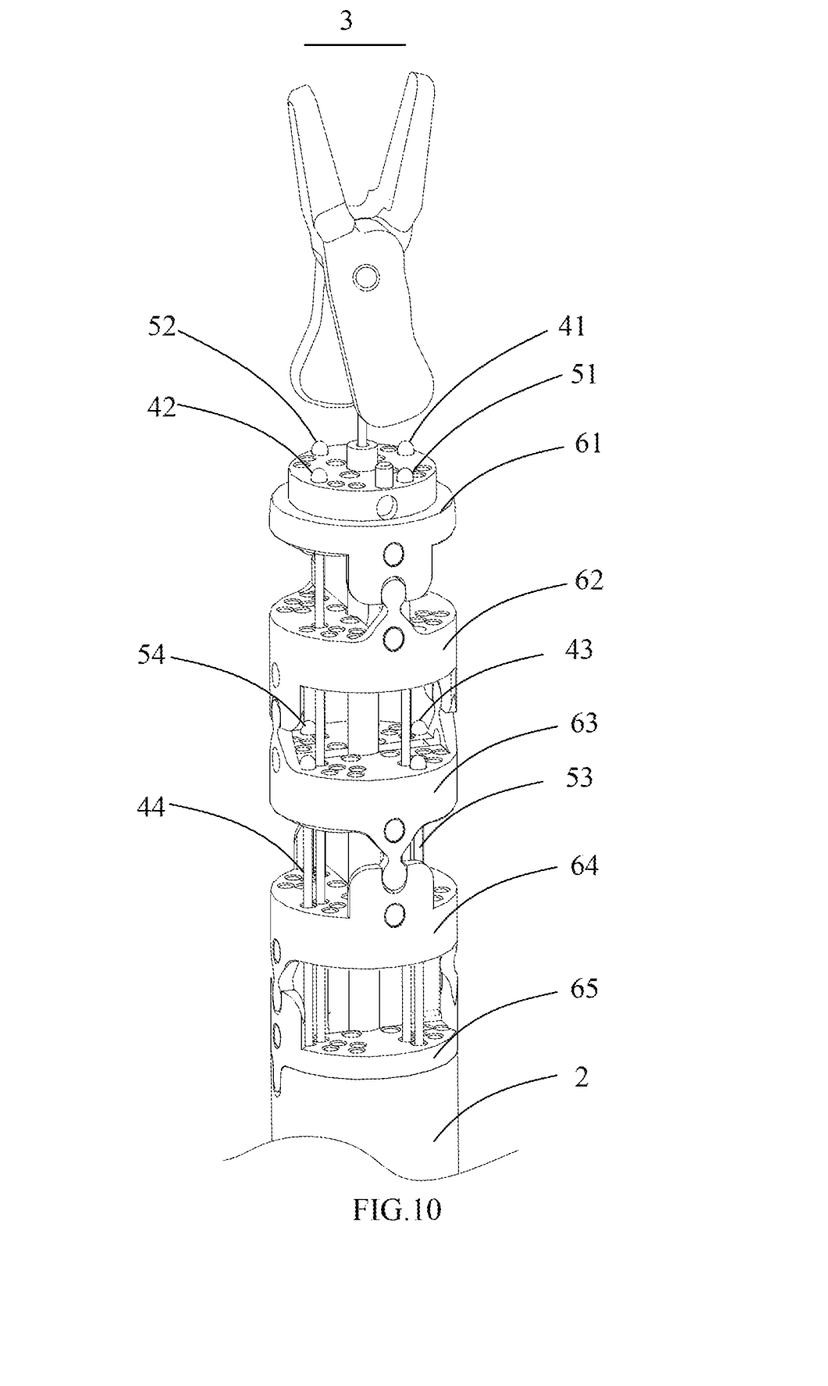
FIG. 10 is a schematic view of an end instrument of the operating arm in FIG. 1 according to a second embodiment.
Figure 11:
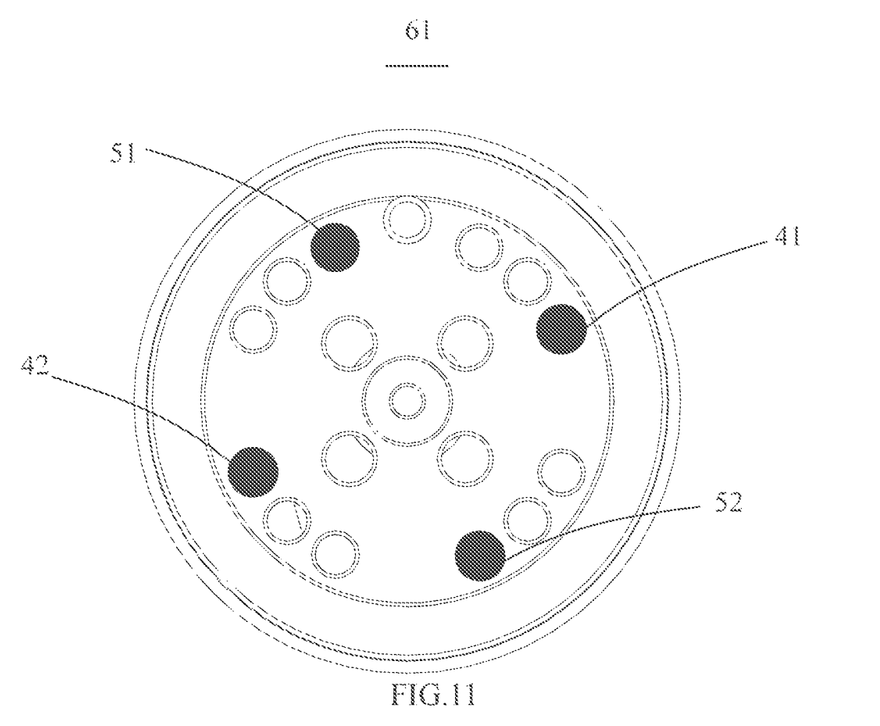
FIG. 11 is a schematic view of a first connecting unit of the end instrument in FIG. 10 from a top view according to an embodiment.
Figure 12:
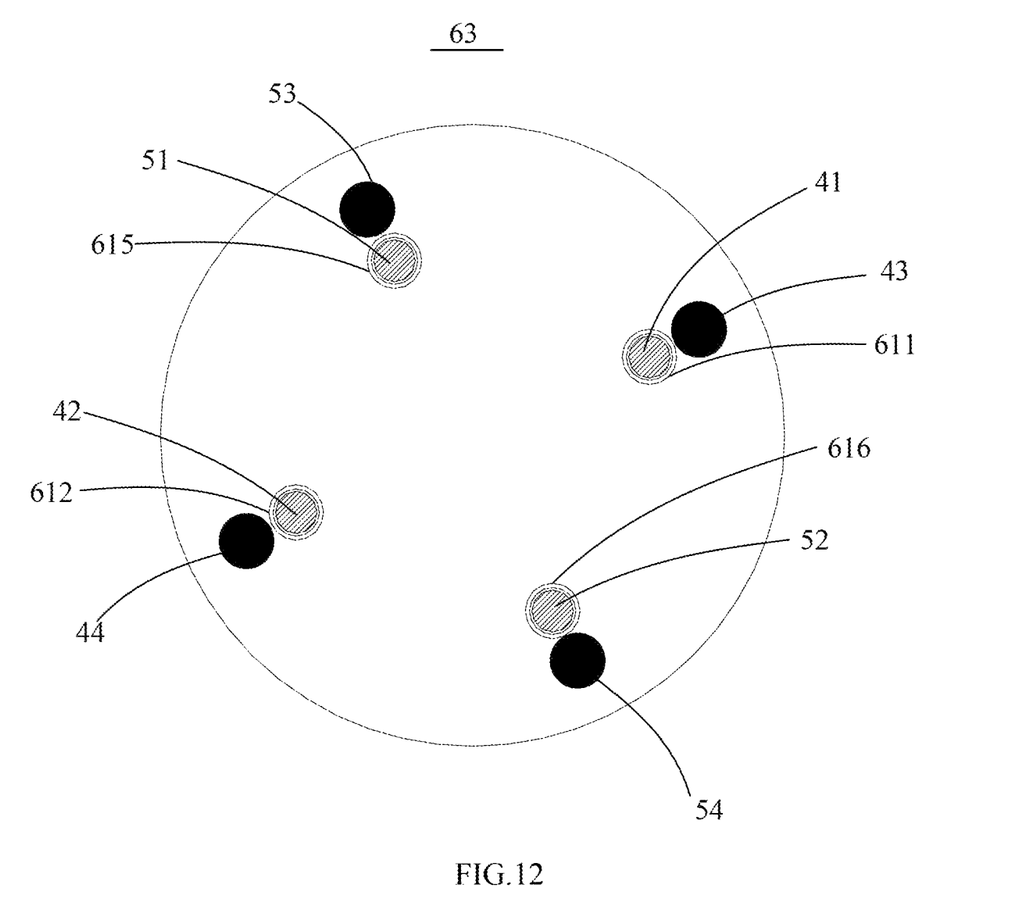
FIG. 12 is a schematic view of a third connecting unit of the end instrument in FIG. 10 from a top view according to an embodiment.

In another embodiment, as shown in FIGS. 10 to 12, the first driving wire 41, the second driving wire 42, the fifth driving wire 51, and the sixth driving wire 52 each have a spherical structure corresponding to the end position of the connecting assembly. The third driving wire 43, the fourth driving wire 44, the seventh driving wire 53, and the eighth driving wire 54 each have a spherical structure corresponding to the end position of the connecting assembly. That is, the first driving wire 41, the second driving wire 42, the fifth driving wire 51, the sixth driving wire 52, the third driving wire 43, the fourth driving wire 44, the seventh driving wire 53, and the eighth driving wire 54 each are independent driving wires. In this way, the mounting process of the driving wires is reduced, which is more convenient to mount the driver wire, thereby improving the installation efficiency. It will be appreciated that the diameter of the end spherical structure of each driving wire is greater than the diameter of each through hole.

The operating arm 100 and the surgical robot provided herein, by providing a first rotatable shaft 111 and a second rotatable shaft 112 having different diameters, and using the first group of driving wires 4 starting from the first rotatable shaft 111 and terminating at the first position of the connecting assembly 6, and the second group of driving wire 5 starting at the second rotatable shaft 112 and terminating at the second position of the connecting assembly 6, such different starting positions and different terminating positions facilitate the driving wires drive the connecting assembly 6 move different degrees in different directions, thereby implementing the end instrument 3 is driven by the first group of driving wire 4 and the second group of driving wire 5 to realize movement of the corresponding degrees of freedom, thereby increasing the flexibility of the operating arm 100 during operation.

The above-described embodiments have only expressed several embodiments of the present application, which are described in more detail and detail, but are not therefore to be construed as limiting the scope of the present application. It should be noted that variations and modifications may be made to one of ordinary skill in the art without departing from the spirit of the present application, all of which fall within the scope of the present application. Therefore, the scope of the appended claims should be accorded the broadest interpretation so as to encompass all such modifications and similar arrangements.

The invention claimed is:

1. An operating arm, comprising successively connected a driving cartridge, a link, an end instrument, and a first group of driving wire and a second group of driving wire penetrating the link, the end instrument comprising a connecting assembly connected to the link and an end effector connected to the connecting assembly, the connecting assembly comprising a first connecting unit coupled to the end effector, a second connecting unit coupled to the first connecting unit, a third connecting unit coupled to the second connecting unit, a fourth connecting unit coupled to the third connecting unit, and a fifth connecting unit having one end coupled to the fourth connecting unit and another end coupled to the link, two of the first, the second, the third, the fourth, and the fifth connecting units rotatable relative to each other about a rotation axis, and the rotation axis of each connecting unit joint assembly nonparallel to the rotation axis of an adjacent connecting unit; and the driving cartridge comprising a base connected to the link, and at least two driving shaft assemblies arranged on the base, each of the at least two driving shaft assemblies comprising a first rotatable shaft arranged on the base, and a second rotatable shaft arranged on the first rotatable shaft and coaxially rotatable with the first rotatable shaft, the first group of driving wire comprising a first driving wire, a second driving wire, a third driving wire, and a fourth driving wire all wound around one of the at least two driving shaft assemblies, the first driving wire and the second driving wire both starting from the first rotatable shaft, the third driving wire and the fourth driving wire both starting from the second rotatable shaft, the second group of driving wire comprising a fifth driving wire, a sixth driving wire, a seventh driving wire, and an eighth driving wire all wound around another one of the at least two driving shaft assemblies, the fifth driving wire and the sixth driving wire both starting from the first rotatable shaft, the seventh driving wire and the eighth driving wire both starting from the second rotatable shaft, the first driving wire, the second driving wire, the fifth driving wire, and the sixth driving wire all terminating at the first connecting unit, the third driving wire, the fourth driving wire, the seventh driving wire, and the eighth driving wire all terminating at the third connecting unit, thereby the first group of driving wire and the second group of driving wire drives the end instrument to move in a direction corresponding to a degree of freedom during rotation of the at least two driving shaft assemblies.

2. The operating arm of claim 1, wherein the rotation axis between the first connecting unit and the second connecting unit is parallel with the rotation axis between the third connecting unit and the fourth connecting unit, the rotation axis between the second connecting unit and the third connecting unit is parallel with the rotation axis between the fourth connecting unit and the fifth connecting unit, and the rotation axis between the first connecting unit and the second connecting unit is perpendicular to the rotation axis between the second connecting unit and the third connecting unit.

3. The operating arm of claim 2, wherein the at least two driving shaft assemblies comprises a pitch driving shaft assembly and a yaw driving shaft assembly, the pitch driving shaft assembly comprises a first thick shaft arranged on the base and a first thin shaft arranged on the first thick shaft and coaxially rotated with the first thick shaft, the first driving wire and the second driving wire both start from the first thick shaft with different winding directions, the third driving wire and the fourth driving wire both start from the first thin shaft with different winding directions; and the yaw driving shaft assembly comprises a second thick shaft arranged on the base and a second thin shaft arranged on the second thick shaft and coaxially rotated with the second thick shaft, the fifth driving wire and the sixth driving wire both start from the second thick shaft with different winding directions, and the seventh driving wire and the eighth driving wire both start from the second thin shaft with different winding directions.

4. The operating arm of claim 3, wherein the pitch driving shaft assembly drives the end instrument to implement pitch degrees of freedom of movement, a change in length of the first driving wire is equal to a sum of a first change in length and a second change in length, the first change in length is a change in length of a portion of the first driving wire between the first connecting unit and the second connecting unit, the second change in length is a change in length of a portion of the first driving wire between the third connecting unit and the fourth connecting unit;
 a change in length of the second driving wire is equal to a sum of a third change in length and a fourth change in length, the third change in length is a change in length of a portion of the second driving wire between the first connecting unit and the second connecting unit, the fourth change in length is a length variation of a portion of the second driving wire between the third connecting unit and the fourth connecting unit; and
 a fifth change in length of the third driving wire is equal to a sixth change in length of the fourth driving wire, the fifth change in length is a change in length of a portion of the third driving wire between the third connecting unit and the fourth connecting unit, the sixth change in length is a change in length of a portion of the fourth driving wire between the third connecting unit and fourth connecting unit.

5. The operating arm of claim 4, wherein the first change in length is equivalent to the third change in length, the second change in length is equivalent to the fourth change in length.

6. The operating arm of claim 4, wherein a ratio of a diameter of the first thick shaft and a diameter of the first thin shaft is equivalent to a ratio of the change in length of the first driving wire and the fifth change in length of the third driving wire; or equivalent to a ratio of the change in length of the second driving wire and the sixth change in length of the fourth driving wire.

7. The operating arm of claim 3, wherein the yaw driving shaft assembly drives the end instrument to implement yaw degrees of freedom of movement, a change in length of the fifth driving wire is equal to a sum of a seventh change in length and an eighth change in length, the seventh change in length is a change in length of a portion of the fifth driving wire between the second connecting unit and the third connecting unit, the eighth change in length is a change in length of a portion of the fifth driving wire between the fourth connecting unit and the fifth connecting unit;
 a change in length of the sixth driving wire is equal to a sum of a ninth change in length and a tenth change in length, the ninth change in length is a change in length of a portion of the sixth driving wire between the second connecting unit and the third connecting unit, the tenth change in length is a change in length of a portion of the sixth driving wire between the fourth connecting unit and the fifth connecting unit; and
 an eleventh change in length of the seventh driving wire is equivalent to a twelfth change in length of the eighth driving wire, the eleventh change in length is a change in length of a portion of the seventh driving wire between the fourth connecting unit and the fifth connecting unit, and the twelfth change in length is a change in length of a portion of the eighth driving wire between the fourth connecting unit and the fifth connecting unit.

8. The operating arm of claim 7, wherein the seventh change in length is equivalent to the ninth change in length, and the eighth change in length is equivalent to the tenth change in length.

9. The operating arm of claim 7, wherein a ratio of a diameter of the second thick shaft and a diameter of the second thin shaft is equal to a ratio of the change in length of the fifth driving wire and the eleventh change in length of the seventh driving wire; or equal to a ratio of the change in length of the sixth driving wire and the twelfth change in length of the eighth driving wire.

10. The operating arm of claim 1, wherein the first driving wire and the second driving wire are arranged on the first connecting unit and oppositely surrounding an axis of the link, the fifth driving wire and the sixth driving wire are arranged on the first connecting unit and oppositely surrounding the axis of the link.

11. The operating arm of claim 10, wherein the first driving wire and the fifth driving wire form a continuous driving wire, and the second driving wire and the sixth driving wire form a continuous driving wire.

12. The operating arm of claim 11, wherein the first driving wire, the second driving wire, the fifth driving wire, and the sixth driving wire each have a sphere structure at an end of the connecting assembly.

13. The operating arm of claim 1, wherein the third driving wire and the fourth driving wire are arranged on the third connecting unit and oppositely surrounding an axis of the link, the seventh driving wire and the eighth driving wire are arranged on the third connecting unit and oppositely surrounding the axis of the link.

14. The operating arm of claim 13, wherein the third driving wire and the seventh driving wire are at a complete first continuous driving wire; and/or the fourth driving wire and the eighth driving wire are at a complete second continuous driving wire.

15. The operating arm of claim 14, wherein the third connecting unit comprises a first resident hole and a second resident hole arranged between the third driving wire and the seventh driving wire; the first continuous driving wire comprises a first connecting wire connecting the third driving wire and the seventh driving wire, one end of the first connecting wire is connected to the third driving wire, the other end of the first connecting wire extending the first resident hole and the second resident hole is connected to the seventh driving wire.

16. The operating arm of claim 14, wherein the third connecting unit comprises a third resident hole and a fourth resident hole arranged between the fourth driving wire and the eighth driving wire; the second continuous driving wire comprises a second connecting wire connecting the fourth driving wire and the eighth driving wire, one end of the second connecting wire is connected to the fourth driving wire, the other end of the second connecting wire extending the third resident hole and the fourth resident hole is connected to the eighth driving wire.

17. The operating arm of claim 13, wherein the third driving wire, the fourth driving wire, the seventh driving wire, and the eighth driving wire each have a sphere structure at an end of the connecting assembly.

18. The operating arm of claim 13, wherein the first driving wire is adjacent to the third driving wire, the second driving wire is adjacent to the fourth driving wire, the fifth driving wire is adjacent to the seventh driving wire, the sixth driving wire is adjacent to the eighth driving wire respectively, and the third driving wire, the fourth driving wire, the seventh driving wire, and the eighth driving wire are located near a periphery of the third connecting unit.

19. A surgical robot, the surgical robot comprising an operating arm, the operating arm comprising successively connected a driving cartridge, a link, an end instrument, and a first group of driving wire and a second group of driving wire penetrating the link,     the end instrument comprising a connecting assembly connected to the link and an end effector connected to the connecting assembly, the connecting assembly comprising a first connecting unit coupled to the end effector, a second connecting unit coupled to the first connecting unit, a third connecting unit coupled to the second connecting unit, a fourth connecting unit coupled to the third connecting unit, and a fifth connecting unit having one end coupled to the fourth connecting unit and another end coupled to the link, two of the first, the second, the third, the fourth, and the fifth connecting units rotatable relative to each other about a rotation axis, and the rotation axis of each connecting unit nonparallel to the rotation axis of an adjacent connecting unit; and     the driving cartridge comprising a base connected to the link, and at least two driving shaft assemblies arranged on the base, each of the at least two driving shaft assemblies comprising a first rotatable shaft arranged on the base, and a second rotatable shaft arranged on the first rotatable shaft and coaxially rotatable with the first rotatable shaft, the first group of driving wire comprising a first driving wire, a second driving wire, a third driving wire, and a fourth driving wire all wound around one of the at least two driving shaft assemblies, the first driving wire and the second driving wire both starting from the first rotatable shaft, the third driving wire and the fourth driving wire both starting from the second rotatable shaft, the second group of driving wire comprising a fifth driving wire, a sixth driving wire, a seventh driving wire, and an eighth driving wire all wound around another one of the at least two driving shaft assemblies, the fifth driving wire and the sixth driving wire both starting from the first rotatable shaft, the seventh driving wire and the eighth driving wire both starting from the second rotatable shaft, the first driving wire, the second driving wire, the fifth driving wire, and the sixth driving wire all terminating at the first connecting unit, the third driving wire, the fourth driving wire, the seventh driving wire, and the eighth driving wire all terminating at the third connecting unit, thereby the first group of driving wire and the second group of driving wire drives the end instrument to move in a direction corresponding to a degree of freedom during rotation of the at least two driving shaft assemblies.

\* \* \* \* \*